(12) United States Patent
Gadient et al.

(10) Patent No.: US 10,362,800 B2
(45) Date of Patent: Jul. 30, 2019

(54) POWDEROUS VITAMIN E FORMULATIONS

(75) Inventors: Martin Gadient, Kaiseraugst (CH);
Thomas Lindemann, Kaiseraugst (CH); Mischa Schwaninger, Kaiseraugst (CH); Karl Manfred Voelker, Kaiseraugst (CH); Kai Urban, Kaiseraugst (CH); Stefanie Kirchen, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 923 days.

(21) Appl. No.: 13/976,696

(22) PCT Filed: Dec. 27, 2011

(86) PCT No.: PCT/EP2011/074084
§ 371 (c)(1),
(2), (4) Date: Nov. 4, 2013

(87) PCT Pub. No.: WO2012/089729
PCT Pub. Date: Jul. 5, 2012

(65) Prior Publication Data
US 2014/0056955 A1    Feb. 27, 2014

(30) Foreign Application Priority Data
Dec. 27, 2010 (CH) .................... 2177/10

(51) Int. Cl.
| | | |
|---|---|---|
| *A23L 1/302* | (2006.01) | |
| *A61K 8/02* | (2006.01) | |
| *A61K 8/67* | (2006.01) | |
| *A23P 10/43* | (2016.01) | |
| *A61K 9/14* | (2006.01) | |
| *A61K 9/16* | (2006.01) | |
| *A61K 31/335* | (2006.01) | |
| *A61K 8/25* | (2006.01) | |
| *A61Q 19/00* | (2006.01) | |
| *A23K 40/10* | (2016.01) | |
| *A23K 20/174* | (2016.01) | |
| *A23L 33/15* | (2016.01) | |

(52) U.S. Cl.
CPC .......... *A23P 10/43* (2016.08); *A23K 20/174* (2016.05); *A23K 40/10* (2016.05); *A23L 33/15* (2016.08); *A61K 8/0241* (2013.01); *A61K 8/25* (2013.01); *A61K 8/678* (2013.01); *A61K 9/143* (2013.01); *A61K 9/1611* (2013.01); *A61K 9/1676* (2013.01); *A61K 31/335* (2013.01); *A61Q 19/00* (2013.01); *A61K 2800/10* (2013.01); *A61K 2800/412* (2013.01)

(58) Field of Classification Search
CPC ...... A61K 8/678; A61K 9/143; A61K 9/1611; A61K 31/335; A61K 8/25; A23L 33/15; A23K 40/10
See application file for complete search history.

(56) References Cited

U.S. PATENT DOCUMENTS

| | | | |
|---|---|---|---|
| 3,445,563 A | | 5/1969 | Clegg et al. |
| 3,914,430 A | * | 10/1975 | Cannalonga ........... A61K 9/143 |
| | | | 514/458 |
| 3,962,384 A | | 6/1976 | Cannalonga et al. |
| 4,519,961 A | | 5/1985 | Schumacher et al. |
| 5,120,761 A | | 6/1992 | Finnan |
| 6,086,917 A | * | 7/2000 | Trubiano ................ A23L 2/56 |
| | | | 424/400 |
| 9,247,765 B2 | * | 2/2016 | Deshpande ........... A23L 1/3002 |
| 2001/0014352 A1 | * | 8/2001 | Batra ................... A61K 9/2018 |
| | | | 424/464 |
| 2004/0022821 A1 | | 2/2004 | Holzner et al. |
| 2007/0155649 A1 | | 7/2007 | Holzner et al. |

OTHER PUBLICATIONS

Spectrum MSDS sheet on Vitamin E succinate, 2008, pp. 1-6.*
Barton, Dust Explosion Prevention and Protection, 2002, IChemE, Technology and Engineering, p. 50 and section 4.1.*
Nagy, Development and Control of Dust Explosions, 1983, CRC Press, Technology and Engineering, pages provided.*
International Search Report for PCT/EP2011/074084 dated Jun. 14, 2012.
Traore et al., "Dust explosions: How should the influence of humidity be taken into account?" *Process Safety and Environment Protection*, vol. 87: 14-20 (2009).

* cited by examiner

*Primary Examiner* — Mina Haghighatian
(74) *Attorney, Agent, or Firm* — Nixon & Vanderhye P.C.

(57) ABSTRACT

The present invention relates to improved vitamin E formulations, as well as to the production of such formulations.

9 Claims, No Drawings

POWDEROUS VITAMIN E FORMULATIONS

This application is the U.S. national phase of International Application No. PCT/EP2011/074084 filed 27 Dec. 2011 which designated the U.S. and claims priority to CH 02177/10 filed 27 Dec. 2010, the entire contents of each of which are hereby incorporated by reference.

The present invention relates to improved vitamin E formulations as well as to the production of such formulations.

The term "vitamin E" in the context of the present patent application covers vitamin E and its esters (such as vitamin E acetate).

Vitamin E formulations are available as different kinds of formulations. They can be liquid and solid. Vitamin E formulations with a high amount of vitamin E are usually used to formulate liquid or solid compositions for the end market. Such end market compositions can be food, feed, personal care products, etc. The formulations disclosed and claimed by the present invention are preferably used in food and feed products as well as in personal care products.

Vitamin E formulations in powderous forms do have explosion hazard due to the small particle size of the powder. Even when the powder contains a prominent amount of larger particles, there is always a certain amount of small particles present. These small particles are responsible for the explosion risk.

Dust explosions are a huge risk in any processes wherein powders are used. Therefore there is a need for powderous formulations with low explosion hazard. But nevertheless the powderous formulations must still have the essential (and advantageous) features of a powder, such as free flowable, easy to transport, easy to dosage etc.

Surprisingly it was found that powderous vitamin E formulations comprising one or more specific compounds and a carrier material do have a low risk of explosion.

Therefore the present application relates to a powderous formulation (I) comprising
  (i) at least 50 weight-% (wt-%), based on the total weight of the powderous formulation, of vitamin E and/or vitamin E derivates, and
  (ii) 0.5 wt-%-8 wt-%, based on the total weight of the powderous formulation, of at least one auxiliary compound selected from the group consisting of aluminium ammonium sulphate, aluminium potassium sulfate, ammonium acetate, ammonium bisulphite, ammonium carbonate, ammonium chloride, ammonium dihydrogen phosphate, ammonium hydrogen carbonate, bentonite, montmorillonite, calcium aluminates, calcium carbonate, calcium silicate, synthetic calcium sulphate dihydrate, calcium sulfate, kaolinitic clays (such as Kaolin), diatomaceous earth, perlite, potassium bisulphite, potassium hydrogen carbonate, potassium sulphate, potassium carbonate, sepiolitic clays, silicic acid, synthetic sodium aluminosilicate, sodium aluminosulfate, sodium bisulphate, sodium carbonate, sodium chloride, sodium hydrogen carbonate, sodium sulphate, vermiculite, calcium carbonate, magnesium carbonate, calcareous marine algae, magnesium oxide, magnesium sulphate, dicalcium phosphate, tri-calcium phosphate, mono-dicalcium phosphate, defluorinated rock-phosphate, monocalcium phosphate, calcium-magnesium phosphate, mono-ammonium phosphate, magnesium phosphate, sodium-calcium-magnesium phosphate, mono-sodium phosphate, glycerol, propylene glycol (E 1520), glyceryl triacetate (E1518), sorbitol (E420), polydextrose, lactic acid and urea, and
  (iii) at least 40 wt-%, based on the total weight of the powderous formulation, of a carrier material.

It is clear that the addition of all the wt-% always adds up to 100.

Vitamin E derivates are usually esters (preferably vitamin E acetate).

In the context of the present invention the specific compounds (ii) are also defined as auxiliary compounds.

Preferably the auxiliary compounds have an average particle size (d 0.5) (in the powder formulation) of 10 µm-100 µm.

The explosion hazard of powders (dusts) is usually measured by a standardized method (EN 13821:2002 (Determination of minimum ignition energy of dust/air mixtures)). This is the method which is used for the determination of all MIE values in this patent application. This method allows to determining the minimum ignition energy (MIE) of a powder. The MIE is the minimum amount of energy required to ignite a combustible vapor, gas or dust cloud, for example due to an electrostatic discharge. MIE is measured in joules (J) or mill joules (mJ).

The average size of the powder particles for the measurement according to the procedure in EN 13821:2002 is ≤63 µm.

All the MIE values in this patent application are determined by using a modified Hartmann tube (type MIKE 3) available from Adolf Kühner AG (Birsfelden, CH). This equipment is specially designed to allow the measurement of very low ignition energies. This is achieved by having different capacitors installed. The capacitors are designed to store the energy of 1 mJ, 3 mJ, 10 mJ, 30 mJ, 100 mJ, 300 mJ and 1000 mJ.

When measuring the MIE of commercially available powderous vitamin E formulations, they are usually in the range of 1-3 mJ. This means that a very low amount of energy is sufficient to initiate an explosion.

On the other hand, formulations according to the present invention have MIE values in the range of 10-1000 mJ (or even more than 1000 mJ).

Therefore the present invention relates to formulations (II), which are formulations (I) with MIE values of 10-1000 mJ (determined by the method of EN 13821:2002). It can be even higher than 1000 mJ.

The formulations according to the present invention are powders. But depending on the process of production as well as the storage conditions, the formulations can comprise some water. The water content is usually below 5 wt-%, based on the total weight of the formulation. Therefore a further embodiment of the present invention relates to vitamin E formulations as described above, wherein 0 to 5 wt-%, based on the total weight of the formulation, of water is present.

Preferably the powderous formulations do not comprise other ingredients/compounds as disclosed above. They do not contain any commonly used stabilisers, surface active ingredients or sugars.

The vitamin E and its esters can be from a natural source or it can be synthesised. Due to the nature of either the isolation process or the process of production, it is possible that traces of side products are present.

The carriers used in the formulations according to the present invention are commonly known and used carrier material. A suitable carrier material is synthetically produced precipitated silica. This carrier consists of porous particles. Other suitable carriers are proteins, starches, lignosulfonates and gums.

Preferred embodiments of the present invention are formulations (III), which comprise
(i) at least 50 wt-%, based on the total weight of the powderous formulation, of vitamin E and/or vitamin E derivates, and
(ii) 0.5 wt-% to 8 wt-%, based on the total weight of the formulation, of at least one compound selected from the group consisting of ammonium dihydrogen phosphate, (purified) diatomaceous earth, potassium hydrogen carbonate, potassium sulphate, potassium carbonate, sodium chloride and sodium hydrogen carbonate, and
(iii) at least 40 wt-%, based on the total weight of the powderous formulation, of a carrier material chosen from the group consisting of synthetically produced precipitated silica, proteins, starches, lignosulfonates and gums.

More preferred are formulation (IV), which are formulations (III) with MIE values of 10-1000 mJ (determined by the method of EN 13821:2002). It can be even higher than 1000 mJ.

A more preferred embodiment of the present invention relates to a formulation (V) consisting of
(i) at least 50 wt-%, based on the total weight of the powderous formulation, of vitamin E and/or vitamin E derivates, and
(ii) 0.5 wt-% to 8 wt-%, based on the total weight of the powderous formulation, of at least one auxiliary compound selected from the group consisting of aluminium ammonium sulphate, aluminium potassium sulfate, ammonium acetate, ammonium bisulphite, ammonium carbonate, ammonium chloride, ammonium dihydrogen phosphate, ammonium hydrogen carbonate, bentonite, montmorillonite, calcium aluminates, calcium carbonate, calcium silicate, synthetic calcium sulphate dihydrate, calcium sulfate, kaolinitic clays (such as Kaolin), diatomaceous earth, perlite, potassium bisulphite, potassium hydrogen carbonate, potassium sulphate, potassium carbonate, sepiolitic clays, silicic acid, synthetic sodium aluminosilicate, sodium aluminosulfate, sodium bisulphate, sodium carbonate, sodium chloride, sodium hydrogen carbonate, sodium sulphate, vermiculite, calcium carbonate, magnesium carbonate, calcareous marine algae, magnesium oxide, magnesium sulphate, dicalcium phosphate, tri-calcium phosphate, mono-dicalcium phosphate, defluorinated rock-phosphate, monocalcium phosphate, calcium-magnesium phosphate, mono-ammonium phosphate, magnesium phosphate, sodium-calcium-magnesium phosphate, mono-sodium phosphate, glycerol, propylene glycol (E 1520), glyceryl triacetate (E1518), sorbitol (E420), polydextrose, lactic acid and urea, and
(iii) at least 40 wt-%, based on the total weight of the powderous formulation, of a carrier material chosen from the group consisting of synthetically produced precipitated silica, proteins, starches, lignosulfonates and gum, and
(iv) 0 to 5 wt-%, based on the total weight of the powderous formulation, of water.

More preferred are formulation (VI), which are formulations (V) with MIE values of 10-1000 mJ (determined by the method of EN 13821:2002). It can be even higher than 1000 mJ.

Furthermore preferred are formulations (VI'), which are formulations (VI) wherein the auxiliary compound has an average particle size (d 0.5) of 10 µm-100 µm.

The average particle sizes are measured by a Malvern Master Sizer 2000. During this laser diffraction measurement, particles are passed through a focused laser beam. These particles scatter light at an angle that is inversely proportional to their size. The angular intensity of the scattered light is then measured by a series of photosensitive detectors. The map of scattering intensity versus angle is the primary source of information used to calculate the particle size. For the measurement of dry materials such as the applied additives, a dry powder feeder (Malvern Scirocco) was used.

An especially preferred embodiment of the present invention relates to a formulation (VII) consisting of
(i) at least 50 wt-%, based on the total weight of the powderous formulation, of vitamin E and/or vitamin E derivates, and
(ii) 0.5 to 8 wt-%, based on the total weight of the powderous formulation, of at least one auxiliary compound selected from the group consisting of ammonium dihydrogen phosphate, (purified) diatomaceous earth, potassium hydrogen carbonate, potassium sulphate, potassium carbonate, sodium chloride, sodium sulphate and sodium hydrogen carbonate,
(iii) at least 40 wt-%, based on the total weight of the powderous formulation, of a carrier material chosen from the group consisting of synthetically produced precipitated silica, proteins, starches, lignosulfonates and gum, and
(iv) 0 to 5 wt-%, based on the total weight of the powderous formulation, of water.

More preferred are formulation (VII), which are formulations (VI) with MIE values of 10-1000 mJ (determined by the method of EN 13821:2002). It can be even higher than 1000 mJ.

Furthermore preferred are formulations (VII'), which are formulations (VII) wherein the auxiliary compound has an average particle size (d 0.5) of 10 µm-100 µm.

To produce a powder according to the present invention (formulations (I), (II), (III), (IV), (V), (VI), (VI'), (VII) and (VII')) it is possible that the vitamin E (and/or vitamin E derivative) is sprayed onto the carrier material and then at least one auxiliary compound is added and the formulation is blended.

It is also possible that the vitamin E (and/or a vitamin E derivative) is sprayed onto a mixture of at least one carrier material and at least one auxiliary compound.

All the above disclosed formulations (I), (II), (III), (IV), (V), (VI), (VI'), (VII) and (VII') can be used as such or in food products, feed products and personal care products.

All the above disclosed formulations (I), (II), (III), (IV), (V), (VI), (VI'), (VII) and (VII') can be used as such in the production of food products, feed products and personal care products.

The invention is illustrated by the following Examples. All temperatures are given in ° C. and all parts and percentages are related to the weight.

EXAMPLES

Example 1

63.3 g precipitated silica was filled into an appropriate blender (Diosna-Blender P1/6, 0.5 l volume) at room temperature (RT). Under carefully blending the silica (100-150 rpm) the temperature was increased to approx. 50° C. during 5-10 minutes. 79.2 g of preheated dl-α-tocopherol-acetate (technical grade, 95.5% dl-α-tocopherol-acetate=Vitamin E derivative)) was sprayed by means of a nozzle onto the silica. This procedure was carried out under mixing (100-150 rpm) within approx. 5 minutes. During this process step the temperature slightly increased to approx. 55° C. The mixture was blended for additional 20 minutes at 50-55° C. (100-150 rpm). Then 7.5 g of potassium hydrogen carbonate as additive (median particle size additive: 414 um) was added and this final mixture was blended for 10 minutes (50-55° C., 100-150 rpm). The obtained free flowing white powder was filled into a container. The powder was analyzed according to the above mentioned EN 13821:2002 and the minimum ignition energy was found to be 10-30 mJ, the vitamin E content was determined by HPLC and found to be 50.9%.

Example 2

63.3 g precipitated silica was filled put into an appropriate mixer (Diosna) at RT. 7.5 g of potassium hydrogen carbonate was added as additive (median particle size additive: 414 um). This mixture was mixed for 5-10 minutes (150 rpm), during this process step the temperature was increased to approx. 50° C.

79.2 g of preheated dl-α-tocopherol-acetate (technical grade, 95.5% dl-α-tocopherol-acetate) was sprayed by means of a nozzle onto the silica-additive mixture. This procedure was carried out under mixing (100-150 rpm) within approx. 5 minutes. During this process the temperature slightly increased to approx. 55° C. The mixture was blended for 20 minutes at 50-55° C. (100-150 rpm).

The powder was analyzed according to EN 13821:2002 and the minimum ignition energy was found to be 10-30 mJ, the vitamin E content was determined by HPLC and found to be 51.0%.

Example 3

63.3 g precipitated silica was filled into an appropriate blender (Diosna) at RT. Under carefully blending the silica (100-150 rpm) the temperature was increased to approx. 50° C. during 5-10 minutes. 79.2 g of preheated dl-α-tocopherol-acetate (technical grade, 95.5% dl-α-tocopherol-acetate) was sprayed by means of a nozzle onto the silica. This procedure was carried out under mixing (100-150 rpm) within approx. 5 minutes. During this process step the temperature slightly increased to approx. 55° C. The mixture was blended for additional 20 minutes at 50-55° C. (100-150 rpm). Then 7.5 g of sodium chloride was added and this final mixture was blended for 10 minutes (50-55° C., 100-150 rpm). The obtained free flowing white powder was filled into a container.

The powder was analyzed according to the above mentioned EN 13821:2002 and the minimum ignition energy was found to be 10-30 mJ, the vitamin E content was determined by HPLC and found to be 50.5%.

Example 4

63.3 g precipitated silica was filled put into an appropriate mixer (Diosna) at RT. 7.5 g of sodium chloride was added as additive. This mixture was mixed for 5-10 minutes (150 rpm), during this process step the temperature was increased to approx. 50° C. 79.2 g of preheated dl-α-tocopherol-acetate (technical grade, 95.5% dl-α-tocopherol-acetate) was sprayed by means of a nozzle onto the silica-additive mixture. This procedure was carried out under mixing (100-150 rpm) within approx. 5 minutes. During this process the temperature slightly increased to approx. 55° C. The mixture was blended for 20 minutes at 50-55° C. (100-150 rpm). The powder was analyzed according to EN 13821: 2002 and the minimum ignition energy was found to be 10-30 mJ, the vitamin E content was determined by HPLC and found to be 50.8%.

Example 5

63.3 g precipitated silica was filled into an appropriate blender (Diosna) at RT. Under carefully blending the silica (100-150 rpm) the temperature was increased to approx. 50° C. during 5-10 minutes. 79.2 g of preheated dl-α-tocopherol-acetate (technical grade, 95.5% dl-α-tocopherol-acetate) was sprayed by means of a nozzle onto the silica. This procedure was carried out under mixing (100-150 rpm) within approx. 5 minutes. During this process step the temperature slightly increased to approx. 55° C. The mixture was blended for additional 20 minutes at 50-55° C. (100-150 rpm). Then 7.5 g of ammonium dihydrogen phosphate (additive) was added and this final mixture was blended for 10 minutes (50-55° C., 100-150 rpm). The obtained free flowing white powder was filled into a container.

The powder was analyzed according to the above mentioned EN 13821:2002 and the minimum ignition energy was found to be 10-30 mJ, the vitamin E content was determined by HPLC and found to be 51.9%.

Example 6

9800 g of a vitamin E preparation containing 54% vitamin E and 46% silicon dioxide was filled into an appropriate blender (Nauta) and 200 g sodium chloride having a average particle size (d 0.5), analysed by laser diffraction, of 54 μm was added and the mix was blended for 10 minutes. The obtained free flowing white powder was filled into a container.

The blend was then air classified in an appropriate apparatus (Alpine Multiprocess unit 100 AFG/50ATP), using an air flow of 60 m3/h and rotation speed of the sifter wheel of 2000 rpm, and the fines collected. Assessed by laser diffraction, the particles averaged 27 μm, sodium chloride content was 16.0%, vitamin E content was 33.4%. The fines were analyzed according to the above mentioned EN 13821:2002 and minimum ignition energy was found to be 30-100 mJ.

The invention claimed is:

1. A powderous formulation comprising:
(i) at least 40 wt-%, based on the total weight of the powderous formulation, of a porous particulate carrier material,
(ii) at least 50 wt-%, based on the total weight of the powderous formulation, of vitamin E coated onto the porous particulate carrier material, and
(iii) 0.5 wt-%-8 wt-%, based on the total weight of the powderous formulation, of at least one auxiliary compound selected from the group consisting of aluminium ammonium sulphate, aluminium potassium sulfate, ammonium acetate, ammonium bisulphite, ammonium carbonate, ammonium chloride, ammonium dihydrogen phosphate ammonium hydrogen carbonate, bentonite, montmorillonite, calcium aluminates, calcium carbonate, calcium silicate, synthetic calcium sulphate di-hydrate, calcium sulfate, kaolinitic clays, diatomaceous earth, perlite, potassium bisulphite, potassium hydrogen carbonate, potassium sulphate, potassium carbonate, sepiolitic clays, silicic acid, synthetic sodium aluminosilicate, sodium aluminosulfate, sodium bisulphate, sodium carbonate, sodium chloride, sodium hydrogen carbonate, sodium sulphate, vermiculite, calcium carbonate, magnesium carbonate, calcareous marine algae, magnesium oxide, magnesium sulphate, dicalcium phosphate, tri-calcium phosphate, dicalcium phosphate, defluorinated rock-phosphate, monocalcium phosphate, calcium-magnesium phosphate, mono-ammonium phosphate, magnesium phosphate, sodium-calcium-magnesium phosphate, monosodium phosphate, glycerol, propylene glycol, glyceryl triacetate, sorbitol, polydextrose, lactic acid and urea, wherein the at least one auxiliary compound has an average particle size (d 0.5) of 54-100 μm in the formulation, and wherein the powderous formulation has a minimum ignition energy (MIE) value according to EN 13821:2002 of 10 to 1000 mJ.

2. The powderous formulation according to claim 1, which further comprises:
(iv) 0 to 5 wt-%, based on the total weight of the powderous formulation, of water.

3. The powderous formulation according to claim 1, wherein the carrier material is selected from the group consisting of synthetically produced precipitated silica, proteins, starches, lignosulfonates and gums.

4. The powderous formulation according to claim 1 wherein the at least one auxiliary compound is selected from the group consisting of ammonium dihydrogen phosphate, purified diatomaceous earth, potassium hydrogen carbonate, potassium sulphate, potassium carbonate, sodium chloride, sodium sulphate and sodium hydrogen carbonate.

5. Food, feed or personal care products comprising a formulation of claim 1.

6. A powderous formulation comprising:
(i) at least 40 wt-%, based on the total weigh of the powderous formulation, of a porous particulate carrier material,
(ii) at least 50 wt-%, based on the total weight of the powderous formulation, of vitamin E coated onto the porous particulate carrier material, and
(iii) 0.5 wt-%-8 wt-%, based on the total weight of the powderous formulation, of sodium chloride as an auxiliary compound having an average particle size (d 0.5) in the formulation of 54 μm to 100 μm, wherein the powderous formulation has a minimum ignition energy (MIE) value according to EN 13821:2002 of 30-100 mJ.

7. The powderous formulation according to claim 6, which further comprises:
(iv) 0 to 5 wt-%, based on the total weight of the powderous formulation, of water.

8. The powderous formulation according to claim 6, wherein the carrier material is chosen from the group consisting of synthetically produced precipitated silica, proteins, starches, lignosulfonates and gums.

9. The powderous formulation according to claim 6, wherein the vitamin E is coated onto a mixture of the particulate porous carrier and sodium chloride.

* * * * *